United States Patent
Langeveld et al.

(10) Patent No.: US 6,867,015 B1
(45) Date of Patent: Mar. 15, 2005

(54) RAPID MICROBIOLOGICAL TEST FOR THE DETECTION OF ANTIBACTERIAL COMPOUNDS

(75) Inventors: Pieter Cornelis Langeveld, Delft (NL); Robert Beukers, Nootdorp (NL); Michiel Wilhelmus Christianus Bommele, Delft (NL); Jacobus Stark, Rotterdam (NL)

(73) Assignee: Gist-Brocades B.V. (NL)

( * ) Notice: Subject to any disclaimer, the term of this patent is extended or adjusted under 35 U.S.C. 154(b) by 0 days.

(21) Appl. No.: 08/704,747

(22) PCT Filed: Feb. 1, 1996

(86) PCT No.: PCT/EP96/00488

§ 371 (c)(1),
(2), (4) Date: Sep. 18, 1996

(87) PCT Pub. No.: WO96/23901

PCT Pub. Date: Aug. 8, 1996

(30) Foreign Application Priority Data

Feb. 1, 1995 (EP) .......................................... 95200243

(51) Int. Cl.⁷ ................................................ C12Q 1/02
(52) U.S. Cl. ......................................... 435/29; 435/32
(58) Field of Search ............................. 435/29, 32, 33, 435/34, 36, 252.1, 253.6, 810, 81

(56) References Cited

U.S. PATENT DOCUMENTS

| | | | | |
|---|---|---|---|---|
| 3,941,658 A | * | 3/1976 | Lameris et al. | 195/103.5 R |
| 4,929,546 A | * | 5/1990 | Mayra-Makinen | 435/29 |
| 4,946,777 A | * | 8/1990 | Lameris et al. | 435/29 |
| 5,008,255 A | | 4/1991 | Edwards et al. | |
| 5,354,663 A | * | 10/1994 | Charm et al. | 435/32 |
| 5,494,805 A | * | 2/1996 | Van Rijn et al. | 435/32 |

FOREIGN PATENT DOCUMENTS

| | | |
|---|---|---|
| CA | 2056581 | 5/1993 |
| DE | 0755456 | 11/2000 |
| EP | 0005891 | 12/1979 |
| EP | 0174477 | 3/1986 |
| EP | 0285792 | 10/1988 |
| EP | 0702087 | 3/1996 |
| WO | 9418343 | 8/1994 |
| WO | 9623901 | 8/1996 |

OTHER PUBLICATIONS

Opposition Proceedings against EP 07/55456 by Charm Sciences.*
Milk and Milk Products, Detection of Inhibitors. International Dairy Federation, Group E 47, Mar. 1991, 2nd edition.*
International Dairy Federation, "Detection of Inhibitors", 3/91 Teststreifen zum Nachweis von Hemmstoffen in Milch Article (7 pgs).
Untersuchung von Lebensmitteln Article 3/87 (4 pages) Milchwissenschaft Milk Science International Article, (5 pgs.) 11/67.
Deutsche Veterinarmedizinische Gellschaft e.V. German Veterinary Medical Society Article (7 pages), Dr. Suneli et al, 1994.

* cited by examiner

Primary Examiner—Ralph Gitomer
(74) Attorney, Agent, or Firm—Muserlian, Lucas and Mercanti

(57) ABSTRACT

The present invention relates to a microbioligcal test method for detecting antibacterial compounds in liquid samples such as milk, meat juice, serum and urine. The method employs an acid-base or redox indicator to detect growth of a test organism and is characterised in that a thermophilic strain of Bacillus or Streptococcus, e.g. Bacillus stearothermophilus var. calidolactis C953, is employed at a concentration of above $10^7$ CFU/ml, preferably between $2 \times 10^7$ and $3 \times 10^8$ CFU/ml.

7 Claims, 2 Drawing Sheets

Test duration versus spore-concentration

Test duration versus spore-concentration

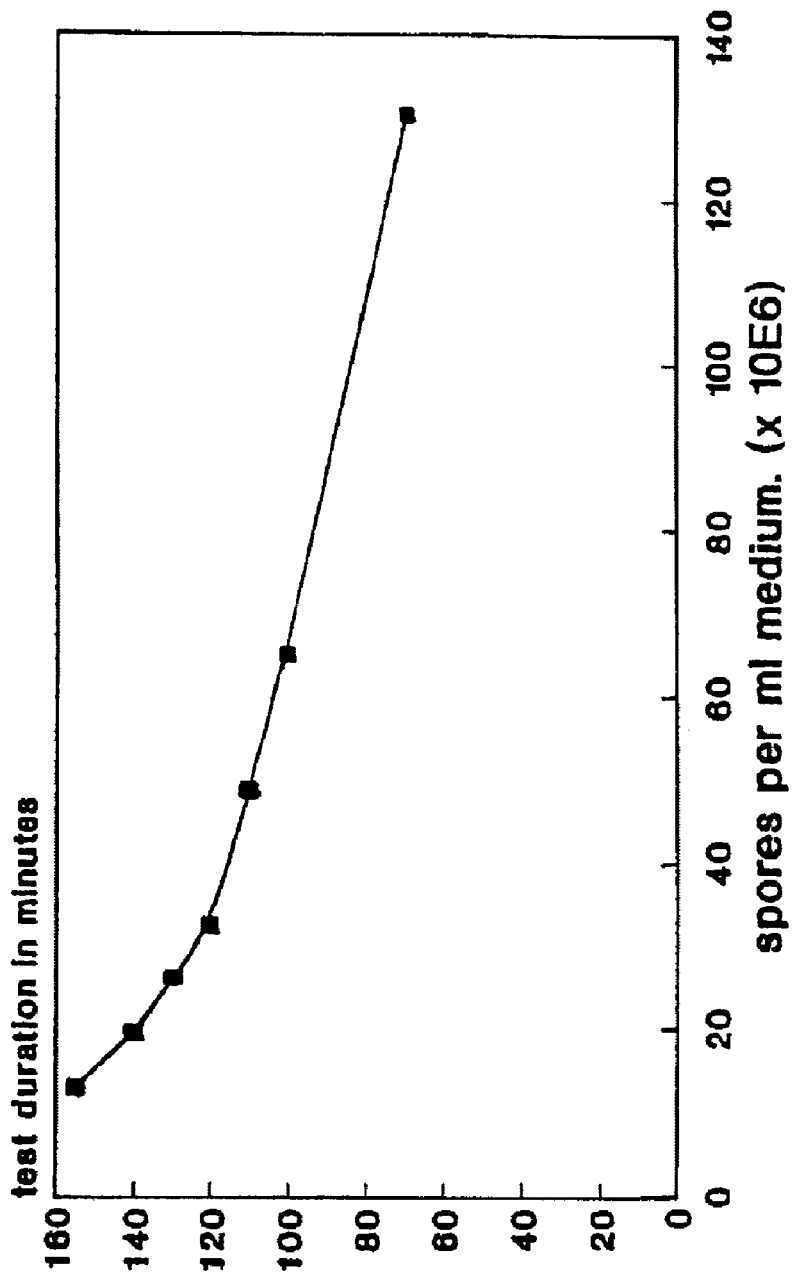

RAPID MICROBIOLOGICAL TEST FOR THE DETECTION OF ANTIBACTERIAL COMPOUNDS

Figure 1:
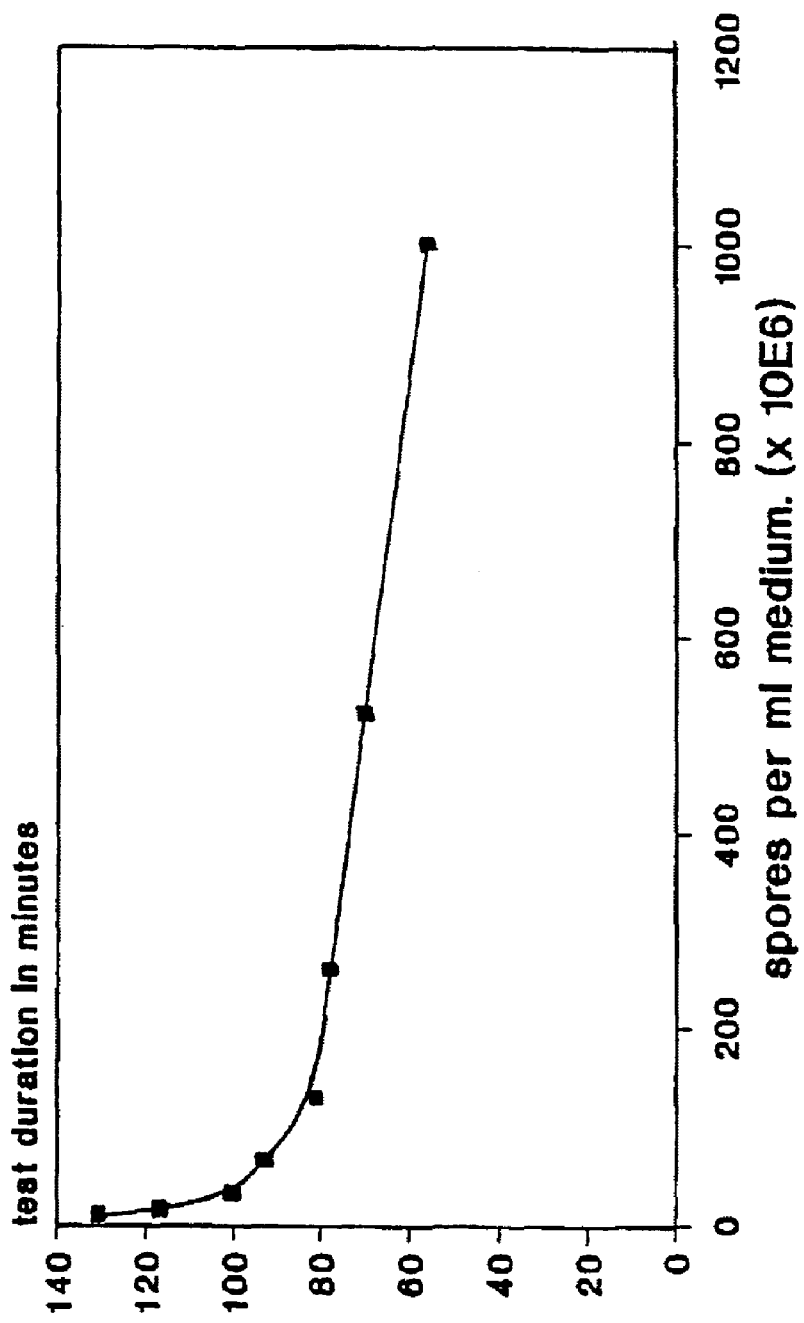

This application is a National Stage of PCT/EP96/00488 filed Feb. 1, 1996 which claims priority to EPO 95200243.4 filed Feb. 1, 1995.

FIELD OF THE INVENTION

This invention relates to a novel microbiological test method for the rapid determination of the presence or absence of antibacterial compounds in liquids such as milk, meat juice, serum and urine. The invention also relates to a unit for the detection of residues of antibacterial compounds in liquid samples and the use of the unit.

DESCRIPTION OF THE PRIOR ART

Microbiological test methods for the determination of antibacterial compounds, particularly residues of antibiotics and chemotherapeutics such as sulphas, in liquid samples such as milk, meat juice, serum and urine have been known for a long time. Examples of such tests have been described in GB-A-1467439, EP 0005891. DE 3613794, CA 2056581 and EP 0285792. These descriptions all deal with ready to use tests that make use of a test organism and will give a result generally within 2½ to 4½, hours by the change of colour of an acid-base or redox indicator added to the test system. The principle is that when an antibacterial compound is present in the sample in a concentration sufficient to inhibit the growth of the test organism the colour of the indicator will stay the same, while when no inhibition occurs the growth of the test organism is accompanied by the formation of acid or reduced metabolites that will change the colour of the indicator.

The known test units mentioned above may include an agar medium inoculated with a suitable test organism, preferably a strain of *Bacillus* or *Streptococcus* and an acid-base indicator or a redox indicator. The suitable test organism and the indicator are introduced into an optionally buffered agar solution, optionally nutrients are added to the solution and optionally substances to change the sensitivity to certain antimicrobial compounds in a positive or a negative way are added to the solution. Finally, the agar solution is allowed to solidity to form the agar medium in such a way that the test organisms stay alive but cannot multiply because of lack of nutrients and/or low temperature. Optionally compounds may be added to the agar medium, e.g. the nutrients or the indicator(s) as a separate source, e.g. as a tablet or a paper disc.

A preferred species of *Streptococcus* for use in conventional microbiological tests for antibacterial compounds is *Streptococcus thermophilus*. A preferred species of *Bacillus* for use in such tests is *Bacillus stearothermophilus*. This species may be employed for this purpose as spores.

In most documents concerning microbiological tests for antibacterial compounds, a very broad concentration of the test organism of $10^5$ to $10^8$–$10^9$ colony forming units (CFU) per ml is mentioned. Examples of such documents are GB-A-1467439, EP 000581, EP 0611001, DE 3429823, U.S. Pat. No. 3,941,658, U.S. Pat. No. 4,946,777 and EP 0285792. However, none of these documents has an example specifying a concentration of test organism higher than $10^7$ CFU/ml This reflects the fact that in practice microbiological tests for antibacterial compounds have previously routinely been carried out with a test organism concentration below $10^7$ CFU/ml. In CA 2056581 (page 11, line 27), it is specifically stated that the concentration of test organism—in this particular case the spores of *Bacillus stearothermophilus*—may vary, but may never exceed a concentration of $10^7$ CFU per ml agar medium.

Thus, up till now, it has been commonly accepted that a test organism concentration of $10^7$ CFU per ml is the maximum concentration that could be used in the type of microbiological tests described in this document. Up till now, it has been commonly thought that use of a higher microorganism concentration in such a test will result in loss of sensitivity for relevant antibacterial compounds.

Of course, a suitable rapid test for antibacterial compounds should among others fulfill the following requirement:

a high sensitivity for a wide range of antibacterial compounds used in practice.

A test with a bacterium concentration of $10^6$ to $10^7$ CFU per ml generally gives a result between 2½ to 4½ hours or even after a longer time. Although a test duration of minimal 1½ hours sometimes is mentioned (for example EP 000581, GB-A-1467439, U.S. Pat. No. 3,941,658, U.S. Pat. No. 4946777) such a test has never been demonstrated in an example or anywhere else.

Up till now, it was not considered possible to carry out a microbiological test for antibacterial compounds with a test duration less than 2½ hours by using a concentration of test organism higher than $10^7$ per ml while retaining good sensitivity for a wide range of antibacterial compounds. The present specification now teaches that, contrary to expectation, such microbiological tests are feasible.

DESCRIPTION OF THE INVENTION

In one aspect, the present invention provides a method for detecting one or more antibacterial compounds in a liquid sample, such as milk, meat juice, serum or urine, which comprises the steps of:

(i) contacting said sample with therein a test microorganism selected from thermophilic strains of *Bacillus* and *Streptococcus*, prior to addition of said sample growth of said test microorganism being prevented;

(ii) providing conditions for said test microorganism whereby in the absence of antibacterial compounds growth of said test microorganism can occur and can be detected; and (iii) detecting the growth of said microorganism after a time sufficient for detection of test microorganism growth in the absence of antibacterial compounds, but during which period detectable test microorganism growth is maintained by a known amount of an antibacterial compound in a test sample; characterised in that said test microorganism is present at above $10^7$ CFU/ml.

Such a test method provides a marked reduction in test duration compared with conventional microbiological tests for antibacterial compounds. While conventional microbiological tests for antibacterial compounds generally give a result between 2½ and 4½ hours, a method described in this document gives a result in less than 2½ hours, e.g 70 minutes or possibly less e.g. 60 minutes or less. This is of extreme importance to the user because the quality of the sample liquid is known more quickly thus allowing an earlier delivery or processing.

Moreover, surprisingly, by employing a microbiological test of the invention with a test organism concentration of more than $10^7$ CFU per ml, a result can be obtained in less than 150 minutes without losing sensitivity. Thus, it has been found possible using a microbiological test of the invention to detect in well below 2½ hours, e.g. as little as 70 minutes, Penicillin G at 0.003 IU/ml in a milk sample (see Examples).

The test microorganism present in the test is preserved under such conditions that they are activated, even after at least one year, when contacted with the test sample.

The test microorganism may be preserved in dispersed form in a solidified medium e.g. solidified agar medium.

According to another embodiment the test microorganism is preserved in concentrated form e.g. in dried form. In case the microorganism is dispersed in solidified medium, the amount or presence of the microorganism is defined as CFU of said microorganism per ml of said medium (CFU/ml). In case the microorganism is present in other forms (e.g. freeze-dried), the amount or presence of the microorganism is defined as CFU's of said microorganism per ml test sample (e.g. milk) added during the method of detection (CFU/ml).

Antibacterial compounds which can be detected in accordance with the present invention are antibiotics and chemotherapeutics like sulpha compounds. A test method of the invention may be used for the detection of antibacterial compounds in a wide range of liquid samples, for example milk, milk products, meat juices, serum, urine, eggs, honey, water and extracts of meat, eggs or honey.

In a further aspect, the invention provides a test unit for carrying out a method of the invention comprising a container holding a solidified agar medium having dispersed therein a test organism selected from thermophilic strains of *Bacillus* and *Streptococcus* at above $10^7$ CFU/ml, said agar medium optionally additionally containing nutrients for growth of said test organism and/or one or more components for detection of said growth. Examples of containers useful for the purpose of the invention are tubes or blocks with tubular indentations, for example, transparent tubes, single or in a set, or combined in the form of a block of translucent material having a number of holes shaped therein, e.g. microtiter plates.

The agar medium in such a unit may be an optionally buffered agar medium to which is added a test organism, a nutrient source comprising sufficient nutrients to support growth of the test organism, an acid-base indicator or one or more redox indicators and optionally substances to change the sensitivity to certain antimicrobial compounds In a positive or a negative way. All the test components may be incorporated into the initial agar solution used for preparation of the test unit or at least some may be added separately to the agar medium.

Thus, optionally at least part of the nutrients may be subsequently incorporated into the agar medium in the test unit from a separate applied source, for example a tablet or paper disc, placed on the agar medium before carrying out the test. At least one indicator component may also be added separately to the agar medium, e.g. by inclusion in a separate nutrient source. Also a buffer and the test organism may be added as a separate source. The nutrient source and/or one or more indicator components, e.g. redox indicators, may be added to the test sample.

When nutrients and/or indicator(s) and/or the test organism are added to the agar medium or test sample from a separate applied source, e.g. a tablet, measures are preferably taken to avoid moisture transport from the agar medium into the applied additive source. When a tablet is employed for this purpose, this may be done by coating the tablet with a moisture resistant layer, for example a wax, which coating must degrade or melt during the test procedure. A wax having a melting temperature of 35° to 55° C., preferably 40° to 45° C. is suitable.

The nutrients are added to enable the multiplication of the test organism in the absence of antibacterial compounds. Suitable nutrients are for example assimilable carbon sources (e.g. lactose, glucose or dextrose) , assimilable nitrogen sources (e.g. peptone) and sources of growth factors and minerals (e.g. yeast extract).

The growth of the test microorganism can be detected by colour change is of the agar medium or the test sample resulting from the presence of an acid base or redox indicator.

If the indicator used is an acid-base indicator, an indicator for a pH of about 5.5 is suitable, preferably bromocresolpurple or phenolred. Other acid-base indicators may however be used as well.

If it is desired to use a redox indicator or a combination of two or more redox indicators, suitable indicators are e.g. Brilliant Black, Methylene Blue, Toluidine Blue, Nile Blue A, 2,3,5-triphenyltetrazolium, Safranine 0, Indigo Carmin, Thionin, Gallocyanine, Brilliant Crocein MOO, Acid Yellow 38, Acid Orange 51, Acid Blue 120, Basic Blue 3, Azure A, Azure B, Congo Red, 1–10 Phenanthroline, Janus Green B, Brilliant Cresyl Blue. Other redox indicators (redox mediators, redox catalysts and electron carriers) may be used as well. Preferred redox indicators are Brilliant Black, Methylene Blue, Toluidine Blue and Nile Blue A or combinations thereof, e.g. a combination of Brilliant Black and Toluidine Blue.

A suitable test organism for a method of the invention is *Streptococcus thermophilus*, preferably *Streptococcus thermophilus* T101 (DSM 4022, deposited on Mar. 3, 1987).

*Bacillus stearothermophilus* may alternatively be employed. Particularly preferred for use in a method of the invention is *Bacillus stearothermophilus* var. *calidolactis* C953. Strain C953 of *Bacillus stearothermophilus* var. *calidolactis* was deposited with the Laboratory of Microbiology of the Technical University of Delft under the accession number LMD 74.1 in 1974 and with the Centraal Bureau voor Schimmelcultures (CBS), Baarn under the accession number CBS 760.83 in 1983 where the strain is available to the public.

*Bacillus stearothermophilus* var. *calidolactis* C953 and *Streptococcus thermophilus* T101 are very sensitive to antibacterial compounds, especially antibiotics such as penicillins and chemotherapeutics such as sulpha compounds. These microorganisms are fast growing and have the additional is advantage that their optimal growing temperature is high (*Bacillus stearothermolphilus*: between 50° C. and 70° C.; *Streptococcus thermophilus*: between 35° C. and 45° C.). This makes these microorganisms very suitable for a test according to the invention as they cannot grow at storage temperature (e.g. room temperature) and there is little possibility that organisms which are possibly present in the test liquid or which have otherwise been included in the test system would affect the result of the test.

When the test organism is a *Bacillus* strain, it is preferably incorporated into the agar medium in the form of a spore suspension which may be prepared and incorporated into the agar medium prior to solidification by known methods (see, for example, GB-A-1467439). Alternatively, as hereinbefore indicated, the test organism may be added as a separate source, for example by application of a tablet or paper disc to the agar medium.

When the test organism is a *Streptococcus* strain, the bacteria are preferably incorporated into the agar medium in the form of bacterial cells which may be prepared according to known methods (EP 0 285 792).

When the test microorganism is in concentrated form (e.g. freeze-dried form, tablet, paper disc, etc.) the concentrate is measured into a vessel which may be a conventional ampoule, a sealable test tube, a sample bottle, a hole of a block such as a microtiter plate and the like (see for example EP-0285792).

The concentration of test organism in the agar medium is suitably above $10^7$ CFU/ml, but desirably does not exceed $10^{10}$ CFU/ml, e.g. a test organism concentration between $2\times10^7$ and $10^9$ CFU/ml may be employed, preferably $2\times10^7$ to $3\times10^8$ CFU/ml. Most preferably, the test organism concentration in the is between $3\times10^7$ and $2\times10^8$ CFU/ml.

According to a preferred embodiment of the present application, the sensitivity of the test organism is adjustable. The sensitivity may be altered by various means, for example by adding certain substances, by changing the test conditions such as the pH or concentration of buffering substances or agar or by varying the ratio of the volumes of agar and test liquid.

Examples of substances that may be added to the test system to change sensitivity are nucleosides such as adenoside and antifolates such as trimethoprim, ormethoprim and tetroxoprim which improve the sensitivity of the test organism to sulpha compounds. Salts of oxalic acid or hydrofluoric acid may be added to improve the sensitivity to tetracyclines. Cysteine may be added to diminish the sensitivity to penicillins.

Hereinafter the invention will be discussed in more detail for a test comprising the agar medium, however, the skilled in the art will appreciate that these teachings can also be applied for tests without an agar medium.

As hereinbefore indicated, components needed or optionally desirable in the agar medium, including optionally substances to change the sensitivity to certain antibacterial compounds, may be added to an optionally buffered agar solution. The agar solution is allowed to solidify in the test units to form the agar medium in such a way that the test organism stays alive but cannot multiply because of lack of nutrients and/or low temperature. The needed compounds which have not been added to the agar solution prior to solidification have to be added from a separate source, for example a tablet or paper disc.

Needed components are the test organism, one or more indicators and the nutrients. Other compounds, e.g. substances to improve or diminish the sensitivity to certain antibacterial compounds and buffer solutions, are optional.

It is preferred to carry out the process of the present invention in such a way that the test organism does not grow or multiply in the agar medium in the presence of a known minimum amount of an antibacterial compound to be detected. Also the test units, e.g test tubes containing the agar medium, have to be stored in such a way that the test organism, does not multiply in the agar medium. This is generally achieved by depriving the organism of nutrients until the test is carried out or by maintaining the culture (during the production process) and the test units (during storage) at a sufficiently low temperature, preferably between 4° C. and 3° C., more preferably between 40° C. and 15° C., or both.

The test units are preferably closed air-tight during storage in which condition they may be stored for at least several months.

The optionally buffered agar medium containing the test organism and/or the indicator(s) and/or the nutrients and/or certain substances to alter the sensitivity of the test is allowed to solidify in upright test units e.g. tubes.

The units preferably have determined sizes. This is because of the reliability of the test. The height of the agar medium in the test units is of great importance. If an antibiotic is present in the test sample it will diffuse into the agar. The sensitivity of the test is therefore preferably ascertained with variation of the height of the solidified agar in the test unit.

Preferably, the height of the agar medium in the test unit is selected in such a way that the indicator changes its colour when the antibacterial compound to be detected is present in a concentration below a certain value, but does not change its colour when the concentration is above this value. Preferably, the test is arranged to be a test from which one can read whether a certain concentration of an antibacterial compound is present or not. For this, the height of the test unit will preferably be high enough to contain an amount of agar medium and sample corresponding to a height of 3–30 mm, more preferably 5–15 mm. The internal cross-sectional dimension of the test units is preferably 1–20 mm, more preferably 1–14 mm.

The volume of the agar medium in the test unit is determined by the height of the test unit, the internal cross-sectonal dimension of the test unit and the percentage of the volume of the test unit which is filled with the agar medium. The volume of the agar medium is preferably 10 µl–3 ml, more preferably 15 µl–1 ml and most preferably 20 µl–500 µl.

A suitable liquid test sample volume is for example 0.01–0.5 ml. Thus, for example, a test unit of the invention formed by solidifying 0.3 ml agar solution in an upright sterile test tube of internal diameter 9 mm has been found suitable for detecting 0.003 lU/ml Penicillin G in a milk sample.

When spores of *Bacillus stearothermophilus* var. *calidolactis* are used, suitable incubation temperatures are between 55° C. and 70° C., more preferably between 60° C. and 66° C. Incubation can be carried out in any conventional form of incubator, e.g. a waterbath, a block heater, a stove or a dry incubator.

When cells of *Streptococcus thermophilus* are used, suitable incubation temperatures are between 36 and 44° C., more preferably between 38 and 42° C.

As hereinbefore indicated, an incubation period of less than 150 minutes is feasible, e.g. 70 minutes, possibly as little as 60 minutes or even 30 minutes. Such an incubation period is markedly shorter than the incubation period of other conventional microbiological test sytems for antibacterial compounds employing less than $10^7$ CFU's/ml.

A test of the invention is very simple to carry out, so that persons who perform the test do not have to be specially educated. The result is very simple to determine. After the incubation period, the colour of the agar medium containing the indicator shows if test organism growth did occur or not.

All documents mentioned in this application are herein incorporated by reference to the same extent as if each individual application or patent was specifically and individually indicated to be incorporated by reference.

LEGEND TO THE FIGURES

FIG. 1: shows the test duration as a function of the spore concentration for test units of type A employed as in Example IV.

FIG. 2: shows the test duration as a function of the spore concentration for test units of type B employed as in Example V.

EXAMPLE I

Preparation of Test Tubes of Type A to Detect Antibiotics

Test tubes of type A contained an agar medium prepared as follows:

A solution was made of 12 g agar, 9 g sodium chloride and 50 ml of a 0.1 M triethanolamine buffer solution (pH=8.0) in 1000 ml distilled water. An amount of a solution of bromocresolpurple to give a final concentration of 20 mg per 1000 ml was also added. The final solution was sterilized for 20 minutes at 121° C. and cooled to about 60° C.

To this solution different amounts of a suspension of *Bacillus stearothermophilus* var. *calidolactis* C953 spores in distilled water were added to give final concentrations between $10^5$ and $10^{10}$ spores per ml.

Sterile tubes with a diameter of about 9 mm were filled with 0.3 ml of the agar solution under aseptic conditions and immediately sealed, e.g. with aluminium foil. The agar solution in the test tubes was allowed to solidify in the test tubes while the test tubes were held in an upright position.

The tubes were stored at a temperature between 5° C. and 15° C.

EXAMPLE II

Preparation of Test Tubes of Type B to Detect Antibiotics

Test tubes of type B contained an agar medium prepared as follows:

A solution was made of 10 g agar, 9 g sodium chloride, 2 g glucose, 2 g peptone, 2 g tryptone, 4 g yeast extract and 50 ml of a 0.1 M triethanolamine buffer solution (pH=8.0) in 1000 ml distilled water. The final solution was sterilized for 20 minutes at 121° C. and cooled to about 60° C.

An amount of a solution of Brilliant Black to give a final concentration of 80 mg per 1000 ml and an amount of a solution of Toluidine Blue to give a final concentration of 3 mg per 1000 ml were also added.

To this solution different amounts of a suspension of *Bacillus stearothermophilus* var. *caildolactis* C953 spores In distilled water were added to give final concentrations between $10^8$ and $10^{10}$ spores per ml.

Sterile tubes with a diameter of about 9 mm were filled with 0.3 ml of the agar solution under aseptic conditions and Immediately sealed e.g. with an aluminum foil. The agar solution In the test tubes was allowed to solidity in the test tubes while the test tubes were held in an upright position.

The tubes were stored at a temperature between 5° C. and 15° C.

EXAMPLE III

Preparation of Nutrient Tablets

A mixture was made of 100 g dextrose, 160 g Avicel PH101, 50 g tryptose, 14 g yeast extract and 15 g precirol. This mixture was sufficient to prepare about 18000 tablets with a diameter of approximately 3 mm and a thickness of approximately 1.9 mm.

EXAMPLE IV

Carrying out the Test Type A

One of each of the test tubes of type A with different concentrations of *Bacillus stearothermophilus* var. *caildolactis* spores as described in Example I ere opened by removing the seals. A nutrient tablet as described in Example III was added to each of the test tubes. Then 0.1 ml of a fresh cow's milk sample was added to each of the test tubes and the test tubes were immediately placed in a waterbath kept at 64° C.

Observations were made after 30 minutes to 2 hours and 30 minutes. The time at which the colour of the agar medium became yellow was determined. As is shown in FIG. 1, the test duration correlated with the number of spores added to the agar medium.

If at this specific time, the colour of the agar medium was blue, the sample was known to contain a detectable amount of an antibacterial compound (e.g. 0.003 I.U. per ml or more penicillin G). FIG. 1 shows that a test duration reduction to at least 60 minutes is realizable,

EXAMPLE V

Carrying out the Test Type B

The procedure described in example IV was followed except that test tubes of type B were used and no tablet was added to the test tube.

FIG. 2 shows that a test duration reduction to at least 70 minutes is realizable.

EXAMPLE VI

Carrying out the Test Type B

An amount of penicillin G of 0.003 I.U. per ml was added to fresh cow's milk. The control sample contained no penicillin G.

Two of each of the test tubes of type B with concentrations of *Bacillus stearothermophilus* var. *calidolactis* spores as described in Example II were opened by removing the seal. Then 0.1 ml of each of the two milk samples was added to each of the test tubes and the test tubes were immediately placed in a waterbath kept at 64° C.

Observations were made after 30 minutes to 3 hours. The time at which the colour of the agar medium became yellow was determined. As is shown in Table 1, the test duration correlated with the amount of spores added to the agar medium without influencing the sensitivity of the test in a negative way.

Table 1 shows a decreasing test duration down to at least 70 minutes. Even at a test duration of 70 minutes, a concentration of 0.003 I.U. per ml Penicillin G can be detected. Of course also higher concentrations of penicillin G can be detected.

TABLE 1

Sensitivity of test type B at different spore concentrations

| | test duration (minutes) | | | | | | | |
|---|---|---|---|---|---|---|---|---|
| | 180 | 155 | 140 | 130 | 120 | 110 | 100 | 70 |
| | | | | spores/ml medium | | | | |
| | $6.5 \times 10^6$ | $1.3 \times 10^7$ | $2.0 \times 10^7$ | $2.6 \times 10^7$ | $3.3 \times 10^7$ | $4.9 \times 10^7$ | $6.5 \times 10^7$ | $1.3 \times 10^5$ |
| milk without antibiotic | − | − | − | − | − | − | − | − |
| milk with 0.003 IU/ml pen. | + | + | + | + | + | + | + | + |

EXAMPLE VII

Detection of Antibiotics and Sulpha Compounds in Microtiterplates (Test Type C)

For the preparation of the test plates (test type C) the procedure described in Example I was followed except that the nutrients described in Example III (dextrose, tryptose and yeast extract) were not added separately but were added to the initial agar medium in the same concentration as described in Example I. Also together with the buffer solution an amount of trimethoprim solution was added to give a final concentration of 60 μg per litre.

To the wells of sterile microtiterplates 20 μl of the agar solution was added under aseptic conditions. The plates were immediately sealed with aluminium foil.

The plates were stored at a temperature between 5° C. and 15° C.

An amount of penicillin G of 3 ppb was added to fresh cow's milk. Also a milk sample was prepared which contains an amount of sulphadiazine of 100 ppb.

The control sample contained no penicillin G or sulphadiazine.

The microtiterplates were opened by removing the seal. Then 20 μl of each of the three milk samples was added to each of the test plates (duplo) containing different concentrations of *Bacillus stearothermophilus* var. *calidolactis* spores C953. The plates were immediately placed in a waterbath kept at 64° C.

Observations were made after 30 minutes to 150 minutes. The time at which the colour of the agar medium became yellow was determined. As is shown in table 2, the test duration correlated with the amount of spores added to the agar medium without influencing the sensitivity of the test in a negative way.

Even at a test duration of 90 minutes both penicillin G and sulphadiazine can be detected at concentrations of respectively 3 ppb penicillin G and 100 ppb sulfadiazine. Penicillin G (3 ppb) can even be detected at a test duration of 80 minutes.

Of course also higher concentrations of both penicillin G and sulphadiazine can be detected.

TABLE 2

Sensitivity of test type C at different spore concentrations.

| Test duration (minutes) | 140 | 123 | 105 | 90 | 80 |
|---|---|---|---|---|---|
| spores/ml medium | $1.3 \times 10^7$ | $2.5 \times 10^7$ | $5.1 \times 10^7$ | $1.0 \times 10^8$ | $2.0 \times 10^8$ |
| milk without antibiotica | − | − | − | − | − |
| milk with 3 ppb penicillin G | + | + | + | + | + |
| milk with 100 ppb sulphadiazine | + | + | + | + | − |

EXAMPLE VIII

Detection of Antibiotics in Milk (Test Type D)

In this experiment *Streptococcus thermophilus* T101 (DSM 4022) was sed for the determination of antibiotics in milk. *Streptococcus thermophilus* T101 was grown using methods known per se.

An amount of a solution of bromocresolpurple to give a final concentration of 45 per 1000 ml was added to fresh cow's milk.

To part of the fresh cow's milk also an amount of penicillin G of 4 ppb added.

The control sample contained no penicillin G.

To the milk samples different amounts of *Streptococcus thermophilus* T101 were added to give final concentrations between $10^7$ and $10^9$ CFU per ml.

Immediately after preparation of the samples sterile tubes with a diameter of about 9 mm were filled with 0.3 ml of each milk sample (duplo). The tubes were immediately placed in a waterbath kept at 42° C.

Observations were made after 30 minutes to 2 hours and 30 minutes.

The time at which the colour of the agar medium became yellow was determined. As is shown in table 3, the test duration correlated with the amount of cells added to the milk without influencing the sensitivity of the test in a negative way.

Even at a test duration of 80 minutes penicillin G can be detected at a concentration of 4 ppb or higher.

TABLE 3

Sensitivity of test type D at different cell concentrations.

| Test duration (minutes) | 145 | 125 | 103 | 80 |
|---|---|---|---|---|
| cells/ml medium | $3.0 \times 10^7$ | $6.0 \times 10^7$ | $1.3 \times 10^8$ | $2.5 \times 10^8$ |
| milk without antibiotica | − | − | − | − |
| milk with 4 ppb penicillin G | + | + | + | + |

What is claimed is:

1. A method for detecting the presence of penicillin G and of sulfadiazine in a liquid sample, the method consisting of
   contacting said liquid sample with a test microorganism, wherein growth of said test microorganism is prevented prior to said contacting,
   incubating said liquid sample with said test microorganism in an agar medium containing nutrient for an amount of time in the presence of one acid-base or a redox indicator,
   providing conditions for said test microorganism that allow growth of said test microorganism in the absence of antibacterial compounds,
   detecting growth of said test microorganism,
   wherein the test microorganism is *Bacillus Stearothermophilus* and said sample is contacted with greater than $3 \times 10^7$ CFU/ml of said test microorganism and the amount of time is 70 to 120 minutes.

2. A method according to claim 1 wherein said agar medium has been formed from an agar solution containing sufficient nutrients to support growth of said *Bacillus stearothermophilus*.

3. A method according to claim 1 wherein the nutrients for said *Bacillus stearothermophilus* is applied to a solidified agar medium.

4. The method according to claim 1 wherein the test microorganism is dispersed in a solidified agar medium.

5. The method according to claim 4 wherein said agar medium has been formed from an agar solution sufficient nutrients to support growth of said test microorganism.

6. The method according to claim 4 wherein a source of nutrients for said test to said solidified agar medium.

7. The method according to claim 1 wherein the test microorganism prior to said contacting is present in concentrated freeze-dried form.

* * * * *